United States Patent [19]

O'Doherty

[11] 4,031,107

[45] June 21, 1977

[54] METHOD FOR INTRODUCING AMINO GROUPS INTO BENZIMIDAZOLE OR IMIDAZOPYRIDINE COMPOUNDS

[75] Inventor: George O. P. O'Doherty, Greenfield, Ind.

[73] Assignee: Eli Lilly and Company, Indianapolis, Ind.

[22] Filed: Feb. 23, 1976

[21] Appl. No.: 660,210

Related U.S. Application Data

[60] Continuation-in-part of Ser. No. 535,233, Dec. 23, 1974, abandoned, which is a division of Ser. No. 314,882, Dec. 13, 1972, Pat. No. 3,875,173, which is a continuation-in-part of Ser. No. 102,266, Dec. 28, 1970, abandoned.

[52] U.S. Cl. .............................. 260/296 H; 71/92; 424/263; 424/273; 260/294.8 C; 260/309.2
[51] Int. Cl.² .............. C07D 235/14; C07D 471/04
[58] Field of Search ...... 260/296 H, 309.2, 294.8 C

[56] References Cited

UNITED STATES PATENTS

| | | | |
|---|---|---|---|
| 3,875,173 | 4/1975 | Doherty | 260/294.8 C |
| 3,932,428 | 1/1976 | Doherty | 260/295 F |

FOREIGN PATENTS OR APPLICATIONS 777,250    6/1972    Belgium ...................... 260/296 H

OTHER PUBLICATIONS

Takahashi et al., I, Chem. Pharm. Bull., vol. 12, pp. 282–291, (1964).
Takahashi et al., II, Chem. Pharm. Bull., vol. 14, pp. 375–385, (1966).
Chemical Abstracts, vol. 76, abst. no. 53629j (1972), (abst. of German Offen. 2,022,504).

*Primary Examiner*—John D. Randolph
*Attorney, Agent, or Firm*—William E. Maycock; Joseph A. Jones; Everet F. Smith

[57] ABSTRACT

The present invention is a process for the introduction of a nucleophilic group into a benzimidazole or imidazo[4,5-b or c]pyridine ring, which comprises treating a derivative of the corresponding 1-hydroxybenzimidazole or -imidazo[4,5-b or c]pyridine with a nucleophilic reagent. The process can also be used to reduce the 1-hydroxybenzimidazole or -imidazo[4,5-b or c]pyridine.

12 Claims, No Drawings

METHOD FOR INTRODUCING AMINO GROUPS INTO BENZIMIDAZOLE OR IMIDAZOPYRIDINE COMPOUNDS

CROSS-REFERENCE TO RELATED APPLICATION

This is a continuation-in-part of my copending application Ser. No. 525,233, filed Dec. 23, 1974, now abandoned, which is a division of my then copending application Ser. No. 314,882, filed Dec. 13, 1972, now U.S. Pat. No. 3,875,173, which was a continuation-in-part of my then copending application Ser. No. 102,266, filed Dec. 28, 1970, now abandoned.

BACKGROUND OF THE INVENTION

In the last decade, considerable research attention has been given to benzimidazole and imidazo[4,5-b and c]-pyridine compounds, particularly those bearing a 2-(trifluoromethyl) group. These compounds, in general, exhibit herbicidal activity; some of the benzimidazole compounds also exhibit insecticidal activity. However, owing to the presence of the trifluoromethyl group, and any electron-withdrawing substitutions son the benzene or pyridine ring, the electrophilic substitution of the benzene or pyridine portion of the ring system has not been feasible. Also, there has hitherto been no technique for the reduction of optimally substituted 1-hydroxy-2-(trifluoromethyl)benzimidazole and 1-hydroxy-2-(trifluoromethyl)imidazo[4,5-b or c]pyridine compounds to the corresponding desoxy compounds.

In the instance of either reduction or introduction of the nucleophilic substituent, the products are useful, in accordance with prior teachings, as herbicides, and, in the case of some of the benzimidazole compounds, as insecticides. See Belgian Pat. Nos. 676,952 and 732,415, regarding benzimidazoles, and U.S. Pat. No. 3,459,759, regarding imidazo[4,5-b or c]pyridines.

SUMMARY OF THE INVENTION

The present process presents a technique for nucleophilic substitution of the benzene or pyridine ring, and for reduction to the corresponding desoxy compound, by reacting a derivative of the corresponding 1-hydroxybenzimidazole or 1-hydroxyimidazo[4,5-b or c]pyridine with a nucleophilic reagent. The 1-derivative can be an ether or an ester, including a carbamate or sulfonate ester, or the unstable derivative formed in situ by the reaction of the corresponding 1-hydroxybenzimidazole or 1-hydroxyimidazo[4,5-b or c]pyridine with a halide, oxyhalide, thiohalide, oxide, or sulfide of an element of Group VA of the Periodic Table of atomic weight from 30 to 122, both inclusive; or a halide, oxyhalide, or oxide of sulfur.

In general, suitable nucleophilic reagents are compounds which will supply a halide ion, such as iodide, bromide, chloride, or fluoride; compounds which will supply a sulfide ion; and amines, including ammonia and primary and secondary amines having a $K_b$ from $10^{-2}$ to $10^{-11}$. The halide ion can be that in a halogen acid; it can be that in any of the compounds used in deriving the unstable halides, oxyhalides, or thiohalides described above; or it can be the halide of an oxalyl halide or phosgene. The identity of the amine is not critical, except that it be basic in nature.

The reaction results in loss of the entire 1-substituent group and introduction of the nucleophilic substitutent into the benzene ring, or, in some cases, the reaction results in reduction to the corresponding desoxy compound.

DETAILED DESCRIPTION OF THE INVENTION

The process of the present invention is useful generally for the introduction of a nucleophilic substituent into the benzene or pyridine ring of a benzimidazole or imidazo[4,5-b or c]pyridine. It is necessary that the compound bear a 2-$CF_3$ group or other $\alpha,\alpha$-difluorinated group. The presence and identity of substituents on the benzene or pyridine ring is not critical so long as one vacant position remains. It is necessary, however, that the compound bear a 1-substituent group which will constitute a "leaving group" under the conditions of reaction. Thus far, only ethers, esters and the unstable derivatives identified hereinabove have been found to be adequate leaving groups.

Preferred first compounds with which the present process is carried out are those defined as follows:

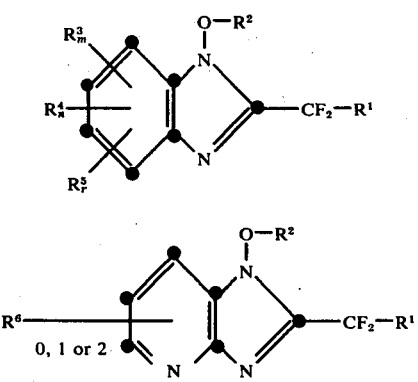

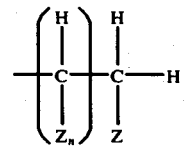

In the above and succeeding formulae throughout the present specification and claims, $R^1$ represents hydrogen, chloro, fluoro, perfluoroalkyl of $C_1$–$C_6$, or radical of the formula $$\left(\begin{array}{c} H \\ | \\ C \\ | \\ Z_n \end{array}\right) \begin{array}{c} H \\ | \\ C \\ | \\ Z \end{array} - H$$

where each Z represents hydrogen or halo and $n$ represents 0 or 1;

$R^2$ represents a derivative group formed by reaction of the corresponding 1-hydroxy compound with a halide, oxyhalide, thiohalide, oxide, or sulfide of an element of Group VA of the Periodic Table of an atomic weight from 30 to 122, both inclusive, or a halide, oxyhalide, or oxide of sulfur; or $R^2$ represents 1. alkyl of $C_1$–$C_8$;
2. alkenyl of $C_2$–$C_8$;
3. cycloalkyl of $C_5$–$5_6$;
4. benzyl;
5. phenethyl;
6. alkanoyl of $C_2$–$C_{16}$;
7. alkenoyl of $C_3$–$C_{16}$;
8. carbamoyl of the formula

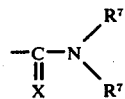

wherein X represents oxygen or sulfur; and one $R^7$ represents phenyl, loweralkyl of $C_1$–$C_4$, or loweralkenyl of $C_2$–$C_4$, and the other $R^7$ represents hydrogen, loweralkyl of $C_1$–$C_4$, or loweralkenyl of $C_2$–$C_4$, subject to the limitation that both $R^7$ groups taken together do not contain more than six carbon atoms; or both $R^7$ groups taken together represent straight-chain alkylene of $C_2$–$C_6$, both inclusive;

9. radical of the formula

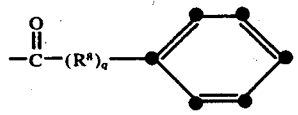

wherein $R^8$ represents methylene, ethylene, or vinylene, and $q$ represents 0 or 1;

10. —$SO_2$—$R^9$ wherein $R^9$ is loweralkyl as above defined, cycloalkyl of $C_5$–$C_6$, phenyl, substituted phenyl as above defined, or benzyl;

11. tetrahydro-2-pyranyl; or 12. radical of the formulae

of

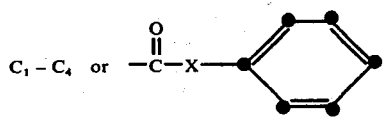

wherein X, as above, is oxygen or sulfur; each $R^3$ independently represents halo; each $R^4$ independently represents nitro, —$CF_3$, —$CF_2Cl$, or —$CF_2H$;

$R^5$ represents cyano or loweralkylsulfonyl of $C_1$–$C_4$;

$m$ represents an integer of from 0 to 3, both inclusive;

$n$ represents an integer of from 0 to 2, both inclusive;

$r$ represents 0 to 1;

and the sum of $m$, $n$, and $r$ is an integer of from 0 to 3 both inclusive; and each $R^6$ represents halogen, nitro, —$CF_3$, —$CF_2Cl$, —$CF_2H$, or loweralkylsulfonyl of $C_1$–$C_4$, subject to the limitation that not more than one $R^6$ represents nitro, —$CF_3$, —$CF_2Cl$, —$CF_2H$, or loweralkylsulfonyl as defined.

A preferred embodiment of the invention is a process suitable for introducing an amino group into a benzimidazole or imidazopyridine compound, which comprises reacting a first compound of one of the formulae

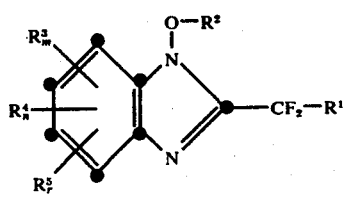

-continued

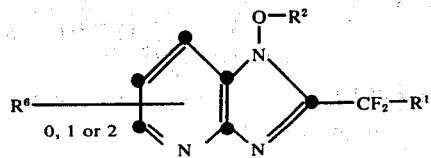

wherein $R^1$ represents hydrogen, chloro, fluoro, perfluoroalkyl of $C_1$–$C_6$, or radical of the formula

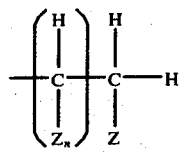

where each Z represents hydrogen or halo and $n$ represents 0 or 1;

$R^2$ represents
1. alkyl of $C_1$–$C_8$;
2. alkenyl of $C_2$–$C_8$;
3. cycloalkyl of $C_5$–$C_6$;
4. benzyl;
5. phenethyl; or
6. tetrahydro-2-pyranyl;

each $R^3$ independently represents halo;

each $R^4$ independently represents nitro, —$CF_3$, —$CF_2Cl$, or —$CF_2H$;

$R^5$ represents cyano or loweralkylsulfonyl of $C_1$–$C_4$;

$m$ represents an integer of from 0 to 3, both inclusive;

$n$ represents an integer of from 0 to 2, both inclusive;

$r$ represents 0 to 1;

and the sum of $m$, $n$, and $r$ is an integer of from 0 to 3, both inclusive; and each $R^6$ represents halogen, nitro, —$CF_3$, —$CF_2Cl$, —$CF_2H$, or loweralkylsulfonyl of $C_1$–$C_4$, subject to the limitation that not more than one $R^6$ represents nitro, —$CF_3$, —$CF_2cl$, —$CF_2H$, or loweralkylsulfonyl as defined; with a nucleophilic reagent selected from the group consisting of ammonia, and primary and secondary amines having a $K_b$ from $10^{-2}$ to $10^{-11}$.

Preferred embodiments are the processes described above wherein the first compound is 1-methoxy-6-chloro-2-(trifluoromethyl)-1H-imidazo[4,5-b]pyridine or 1-methoxy4,6-dinitro-2-(trifluoromethyl)benzimidazole. Further preferred embodiments are the processes wherein the nucleophilic reagent is ammonia, which may be in the form of ammonium hydroxide, tert-butylamine, or n-propylamine. Particularly preferred embodiments are the processes wherein both the first compound and the nucleophilic reagent are chosen from those named immediately above.

Amines having dissociation constants ($K_b$) in the range of $10^{-2}$ to $10^{-11}$ are of adequate basicity, although reaction may be slower when sterically hindered amines or those comprising bulky groups are used. The $K_b$ referred to here is defined in the usual way as [concentration of $OH^-$ion] X [concentration of amine-$H^+$ion]/[concentration of un-ionized amine]. See, e.g., *Basic Physical Chemistry for the Life Sciences*, Williams & Williams (Freeman, 1967), page 140. The $K_b$ is determined at 25° C. in water.

Thus, representative nucleophilic reagents to be employed in the process of the present invention include HCl, HBr, HI, HF, lithium chloride, phosphorus oxychloride, phosphorus oxybromide, phosphorus thiochloride, phosphorus trichloride, phosphorus tribromide, phosphorus oxyfluoride, phosphorus pentasulfide, antimony pentachloride, antimony oxychloride, arsenic tribromide, thionyl chloride, thionyl bromide, ammonium chloride, ammonium bromide, ammonium fluoride, ammonium iodide, methylamine, diethylamine, n-octylamine, tert-butylamine, allylamine, propynylamine, cyclohexylamine, cyclopentylamine, aziridine, aniline, 2-naphthylamine, 2-cyclohexylethylamine, benzylamine, p-chlorobenzylamine, piperidine, hexahydroazepine, 1,2,3,4-tetrahydroquinoline, decahydroisoquinoline, and decahydronaphthylamine.

The identity of the nucleophile determines the course of reaction. Where it is chloride, fluoride, ammonia or primary or secondary amine, rearrangement occurs. Reduction occurs when it is bromide or iodide. To date, good results with ether first compounds have been obtained only with ammonia or primary or secondary amines; and likewise, good results with esters have been obtained only with halide ion. In the case of amines reacting with ester first compounds, it is believed that a competing reaction converts the respective derivative back to the corresponding 1-hydroxy compound, thereby precluding reaction in accordance with the present process.

Where the 1-derivative is that obtained by reaction of the corresponding hydroxy compound with a halide, oxyhalide, or thiohalide of an element of Group VA of the Periodic Table of atomic weight from 30 to 122, both inclusive, or with a halide or oxyhalide of sulfur, that compound itself provides the halide serving as nucleophilic substituent. The reaction course is therefore one of rearrangement where the halide is chloride or fluoride; or reduction where the halide is bromide or iodide. Where the 1-derivative is that obtained by reaction of the corresponding 1-hydroxy compound with a sulfide of the Group VA element (as defined), reduction occurs. In the case of the oxides, for example, the phosphorus or sulfur oxides, reaction serves only to convert the 1-hydroxy into an acceptable leaving group, it being necessary to supply a separate nucleophilic reagent in which case the reaction proceeds in accordance with the identity of the nucleophile supplied.

The mechanism of the present process is not known with certainty. However, it is believed that the first step in the overall sequence is the formation of a noncharged compound comprising as its imidazole portion the following structure:

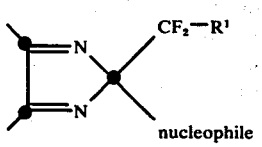
nucleophile

To date, it has not been possible to isolate this compound. It is conjectured that where the nucleophile is bromide or iodide, the compound itself acts as a nucleophilic reagent, attacking solvents or other molecules of the same compound, resulting in reduction. Alternatively, the mechanism may be that of dehalogenation, likewise resulting in reduction. In the alternate course of reaction leading to rearrangement, it is believed that there is charge migration within the ring system of the conjectured intermediate, resulting in attack of a second nucleophile at the position on the benzene or pyridine ring of greatest charge density. The overall reaction scheme can be illustrated as follows, shown for unsubstituted benzimidazole in order to simplify the portrayal. Y represents a nucleophile.

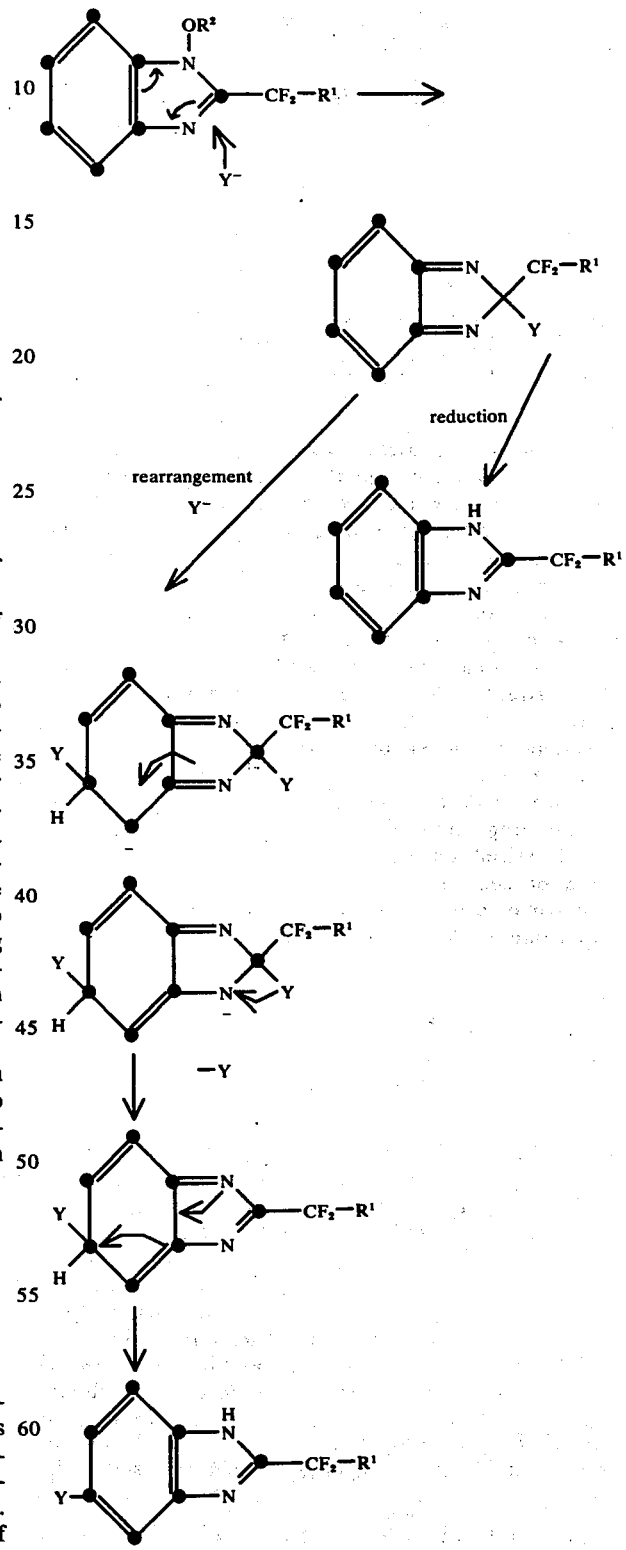

Irrespective of the precise mechanism, however, the reaction represents a singularly useful synthetic technique. Although in some cases, two products M13 one the result of rearrangement, the other, of simple reduction—have been obtained, in general only one product is obtained, and it is obtained in good yield.

The reaction conditions are not critical. In general, the starting 1-hydroxy derivative:

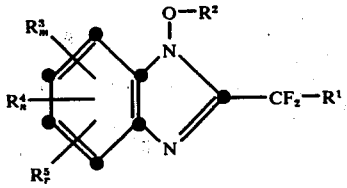

or

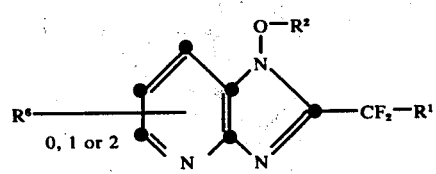

is reacted with a nucleophlic regent. The reaction is generally more conveniently carried out in an inert liquid as reaction medium. Suitable such liquids include lower alkanols; ethers, such as diethyl ether and tetrahydrofuran; hydrocarbons; and acetone. In the case where an oxyhalide of a Group VA element (as defined) or of sulfur is employed as nucleophile, use of a small amount of dimethylformamide, to constitute a Vilsmeier-Haack reagent, is preferred. The reaction goes forward under a wide range of temperatures, such as from 0° to 150°. Generally, however, there is no advantage to the use of temperatures other than room temperatures. The reaction consumes the 1-hydroxy derivative and the nucleophilic reagent in amounts representing equimolecular proportions. Separation, and if desired, purification, are carried out in conventional procedures.

In some cases, the reaction yields product as an imidazolium salt of the nucleophilic reagent involved:

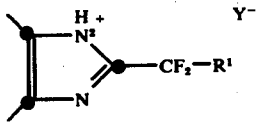

The salt is readily converted back to the imidazole in conventional procedures.

The following examples illustrate the process of the present invention and will enable those skilled in the art to practice the same.

EXAMPLE 1

PREPARATION OF 6-CHLORO-2-(TRIFLUOROMETHYL)-1H-IMIDAZO[4,5-b]PYRIDINE

Dimethylformamide (2 milliliters) was added to 4 grams of 1-hydroxy-2-(trifluoromethyl)-1H-imidazo[4,5-b]pyridine in 10 milliliters of thionyl chloride. The resulting reaction mixture was heated on a steam bath overnight. Solvent was removed and the residue shaken with 50 milliliters of water and filtered. The residue was then taken up in sodium hydroxide solution, filtered and acidified to pH 3, shaken with three 150-milliliter portions of diethyl ether, and dried over magnesium sulfate. Solvent was evaporated, yielding the desired 6-chloro-2-(trifluoromethyl)-1H-imidazo[4,5-b]pyridine, m.p., 290°-2° C., with sublimation from 260° C.

U.S. Pat.No. 3,459,759 identifies this same substance as melting at 293° C. In addition, the product obtained as described in this example was subjected to NMR, I.R., and T.L.C., along with a portion of the same compound prepared as described in the same U.S. Patent. Both samples were essentially indentical in all of the analyses.

EXAMPLE 2

PREPARATION OF 5,6-DICHLORO-2-(TRIFLUOROMETHYL)-1H-IMIDAZO[4,5-b] PYRIDINE 1-(Methylcarbamoyloxy)-6-chloro-2-(trifluoromethyl) -1H-imidazo [4,5-b] pyridine (250 milligrams) in 2.5milliliters of methanol was saturated with HCl. The reaction mixture was permitted to stand for three hours, then poured into water and filtered to separate the desired 5,6-dichloro-2-(trifluoromethyl)-1H-imidazo[4,5-b]pyridine, m.p., 280°-30° C.

EXAMPLE 3

PREPARATION OF 5-AMINO-6-CHLORO-2-(TRIFLUOROMETHYL)-1H-IMIDAZO[[4,5-b] PYRIDINE

1-Methoxy-6-chloro-2-(trifluoromethyl)-1H-imidazo[4,5-b]pyridine (1 gram; 0.004 mole) was dissolved in 15 milliliters of methanol and 2 milliliters of ammonium hydroxide ($d = 0.880$) added. The reaction mixture was permitted to stand for 16 hours, then solvents were removed and the residue crystallized from benzene/acetone, m.p. 242°-4° C. (0.6 gram; about 63 percent yield).

Analysis, Calc.: C, 35.53; H, 1.70; N, 23.68. Found: C, 35.58; H, 1.83; N, 23.43.

EXAMPLE 4:

PREPARATION OF 5,6-DICHLORO-2-(TRIFLUOROMETHYL)-1H-IMIDAZO [4,5-b] PYRIDINE

1-Hydroxy-5-chloro-2-(trifluoromethyl)-1H-imidazo [4,5-b] pyridine (100 milligrams) was mixed with 10milliliters of thionyl chloride and the mixture refluxed on a steam bath for ten hours. The thionyl chloride was then evaporated and the residue, the desired 5,6-dichloro-2-(trifluoromethyl) -1H-imidazo [4,5-b] pyridine product, was shaken with water and separated by filtration, m.p. 222°-24° C.

EXAMPLE 5

PREPARATION OF 6-CHLORO-2-(TRIFLUOROMETHYL)-1H-IMIDAZO [4,5-b] PYRIDINE 1-(Methylsulfonyloxy)-6-chloro-2-(trifluoromethyl)-1H-imidazo [4,5-b] pyridine (20 milligrams) in 0.5 milliliter of acetone was treated with 0.1 gram of sodium iodide in 0.5 milliliter of acetone. The reaction mixture was shaken with ether and bicarbonate solution. The ether portion was dried over magnesium sulfate and evaporated, yielding 10 milligrams (about 73 percent) of 6-chloro-2-(trifluoromethyl)-1H-imidazo [4,5-b] pyridine.

EXAMPLE 6

The same compound prepared as reported in the preceding example was also prepared by reduction with $P_2S_5$. In this preparation, 1.3 grams of 1-hydroxy-6-chloro-2-(trifluoromethyl)-1H-imidazo [4,5-b] pyridine and 1.3 grams of $P_2S_5$ in 10 milliliters of tetrahydrofuran were stirred for sixteen hours. The reaction mixture was then filtered and evaporated. The residue was shaken with 2 percent sodium hydroxide solution, filtered and acidified. A white solid precipitated and was separated. I.R. showed it to be 6-chloro-2-(trifluoromethyl)-1H-imidazo [4,5-b] pyridine.

EXAMPLE 7

PREPARATION OF 4,5,6-TRICHLORO-2-(TRIFLUOROMETHYL) BENZIMIDAZOLE 1-(Methylsulfonyloxy)-5,6-dichloro-2-(trifluoromethyl) benzimidazole (1 gram) in 10 milliliters of methanol was saturated with HCl gas. The reaction appeared to be complete in 15 minutes, and the solvent was then evaporated to obtain, 4,5,6-trichloro-2-(trifluoromethyl) benzimidazole methylsulfonate salt as a residue. It was recrystallized from chloroform, m.p., 164° –5° C.

Analysis, Calc.: C, 28.20; H, 1.57; N, 7.31. Found: C, 28.49; H, 1.88; N, 7.29.

The substance was then taken up in sodium hydroxide solution, converting it to the free 4,5,6-trichloro-2-(trifluoromethyl) benzimidazole. It was extracted with methylene chloride. The residue on evaporation of solvent (m.p., 222° –3° C.) was further identified by comparison (I.R., NMR and T.L.C) with an authentic sample.

EXAMPLE 8

REDUCTION OF 1-(METHYLCARBAMOYLOXY)-5,6-DICHLORO-2-(TRIFLUOROMETHYL) BENZIMIDAZOLE

HBr was passed into a cooled (0° –5° C.) solution of 1.05 grams of 1-(methylcarbamoyloxy)-5,6-dichloro-2 -(trifluoromethyl) benzimidazole in 40 milliliters of methanol. The reaction mixture was permitted to stand for twenty minutes, then evaporated to obtain as a residue 5,6-dichloro-2-(trifluoromethyl) benzimidazole. After recrystallization from chloroform, it melted at 233° –5° C.

EXAMPLE 9

PREPARATION OF 7-CHLORO-4,6-DINITRO-2-(TRIFLUROMETHYL) BENZIMIDAZOLE

Crude 1-hydroxy-4,6-dinitro-2 -(trifluoromethyl)-benzimidazole (about 5 grams) was mixed with about 50 milliliters of thionyl chloride and several drops of dimethylformamide added. The reaction mixture was stirred overnight, then poured slowly into water and filtered. The solid was dissolved in benzene and eluted off a silica column with benzene. As a result of the foregoing operations, the desired 7-chloro-4,6-dinitro-2-(trifluoromethyl) benzimidazole product was obtained, m.p., 189° –91° C.

Analysis, Calc.: C, 30.94; H, 0.65; N, 18.04. Found: C, 30.85; H, 0.86; N, 18.04.

EXAMPLE 10

PREPARATION OF 5-tert-BUTYLAMINO-6-CHLORO-2-(TRIFLUOROMETHYL)-1H- IMIDAZO [4,5-b] PYRIDINE 1-Methoxy-6-chloro-2-(trifluoromethyl)-1H-imidazo [4,5-b] pyridine (2.0 grams) was mixed with tert-butylamine (5 milliliters) in 10 milliliters of diethyl ether. The reaction mixture was permitted to stand for eight days; then solvent was evaporated and the residue taken up in 8 milliliters of chloroform, permitted to stand for two hours, and filtered to separate the desired 5-tert-butylamino-6-chloro-2-(trifluoromethyl)-1H-imidazo [4,5-b] -pyridine, m.p., 252° –4° C.

Analysis, Calc.: C, 45.25; H, 4.12; N, 19.20. Found: C, 45.25; H, 4.23; N, 19.23.

EXAMPLES 11–12

In accordance with the foregoing teachings, 1-hydroxy-4-chloro-6nitro-2-(trifluoromethyl) benzimidazole was reacted with thionyl chloride, resulting in introduction of a 5-chloro substituent.

Also, 6-chloro-2-(trifluoromethyl)-1H-imidazo [4,5-b] pyridine was prepared by reduction of 1-hydroxy-6-chloro-2-(trifluoromethyl)-1H-imidazo [4,5-b] pyridine with thionyl bromide.

EXAMPLE 13

PREPARATION of 5-AMINO-6-CHLORO-2(TRIFLUOROMETHYL)-1H-IMIDAZO [4,5-b] PYRIDINE

A 2.5 g. portion of 6-chloro-1-methoxy-2-(trifluoromethyl)-1-H-imidazo [4,5-b] pyridine was dissolved in 25 ml. of methanol, and the solution was saturated with gaseous ammonia. The reaction mixture was stirred at ambient temperature for 2 hours, and additional ammonia was periodically bubbled through the liquid phase. The solvent was then removed under vacuum, and the solid residue was taken up in ethyl ether and the solution was stirred with anhydrous magnesium sulfate and charcoal. The solids were then removed by filtration, and the filtrate was evaporated to dryness to yield about 2 g. of 5-amino-6-chloro-2-(trifluoromethyl)-1H-imidazo [4,5-b] pyridine, which was recrystallized from chloroform-methanol. The purified product melted at 241° –242° C. , and it was identified conclusively by infrared, nuclear magnetic resonance, mass spectroscopy and elemental microanalysis. The analytical results were as follows.

Analysis, Calc.: C, 35.54; H, 1.70; N, 23.68. Found: C, 35.73; H, 1.74; N, 23.83.

EXAMPLE 14

PREPARATION OF 4,6-DINITRO-7-PIPERIDINO-2-(TRIFLUOROMETHYL) BENZIMIDAZOLE

A 450 mg. portion of 1-methoxy-4,6-dinitro-2-(trifluoromethyl) benzimidazol was dissolved in methanol, and 150mg. of piperidine was added at room temperature. The reaction mixture was constantly stirred, and the progress of the reaction was monitored by thin-layer chromatography. After about 3 hours, the solvent was evaporated under vacuum, and the residue was taken up in water and acidified to pH 3. The mixture was then extracted with ethyl acetate, and the product was isolated by chromatography of the organic layer, using chloroform as the eluent. The product was recrystallized from ethanol-water, and was identified as 4,6-dinitro-7-piperidino-2-(trifluoromethyl) benzimidazole, m.p. 207°–209° C., by nuclear magnetic resonance analysis and elemental microanalysis, the results of which follow. The yield was about 70 mg.

Analysis, Calc.: C, 43.46; H, 3.37; N, 19.49. Found: C, 43.66; H, 3.53; N, 19.75.

As noted hereinabove by reference to prior art patents, all of the compounds prepared by the process of the present invention are useful as herbicides, and some of the compounds (see especially Belgian Pat. No. 732.415) are useful as insecticides. In addition, those of the products of the present process wherein chlorine or fluorine is introduced can be reacted further to introduce yet other groups, e.g., amino groups. Similarly, an introduced amino group will undergo further reaction. Those products which are of the following formula

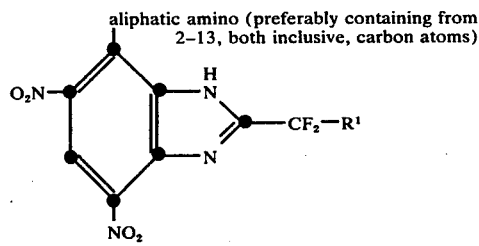

whether the amino group be introduced directly, or indirectly via chlorine introduction and subsequent amination, are useful as insecticides.

The compounds to be employed as starting materials in the process of the present invention are themselves readily synthesized. 1-Hydroxy compounds in both the benzimidazole and 1H imidazo [4,5-b and c] pyridine series are prepared by the reduction of a precursor of the formula

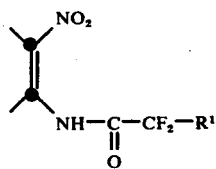

The reaction is believed to go through several intermediates which are not isolable, but yields as product the desired corresponding 1-hydroxybenzimidazole or 1H-imidazo [4,5-b or c] pyridine compound. The reaction conditions are not critical; however, it is generally preferred to employ as reducing agent two moles of hydrogen per mole of the nitropyridineamine, in the presence of a minor amount of a catalyst comprising a noble metal, preferably palladium. In a representative synthesis, 1-hydroxy-6-chloro-2-(trifluoromethyl)-1H-imidazo [4,5-b] pyridine was prepared as follows:

5-Chloro-3-nitro-2-(trifluoroacetamido) pyridine (2.0 grams) was hydrogenated with two mole equivalents of hydrogen in ethanol containing 0.5 gram of 5 percent palladium or carbon. The resulting reaction mixture was filtered and evaporated to separate the desired 6-chloro-1-hydroxy-2-(trifluoromethyl)-1H-imidazo [4,5-b] pyridine compound which, after recrystallization from benzene, melted at 268°–70° C.

Analysis, Calc.: C, 35.39; H, 1.27; N, 17.69. Found: C, 35.59; H, 1.45; N, 17.77.

Those of the compounds to be employed as starting materials which are esters or ethers are prepared in conventional procedures for such derivatization of hydroxy compounds.

Most generally, the ester and ether derivatives are prepared by the reaction of the corresponding 1-hydroxy-compounds:

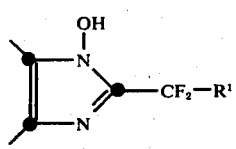

with a halide of the formula $R^2-X$, where X is halo, in the presence of an alkali metal carbonate or other hydrogen halide acceptor. An inert liquid reaction medium can be used. The reaction proceeds under a wide range of temperatures, but is preferably conducted at temperatures of from −20° C. to the reflux temperature. Separation, and, if desired, purification, are carried out in conventional procedures.

While the foregoing is the most general method, other methods are convenient and may be preferred for some of the compounds. Thus, those carbamates of the formula

or loweralkenyl are more readily prepared by reacting the corresponding 1-hydroxy compound with an isocyanate. The reaction is conducted in conventional procedures.

Likewise, the carboxylic ester compounds of the present invention other than the carbamate esters are often preferably prepared by reacting the desired carboxylic acid as its anhydride with the corresponding 1-hydroxy compound.

Furthermore, in the case of the present compounds which are ethers, preparation is sometimes preferably carried out by reaction of the 1-hydroxy compound with an olefin or an alkyne. This is particularly preferred in the case of the tetrahydro-2-pyranyl and vinyl ethers.

Yet other synthetic techniques can be used in the preparation of the first compounds of the present invention examples are the use of N,N' -carbonyldiimidazole or N,N' -dicyclohexylcarbodiimide (See *Reagents for Organic Synthesis*, Fieser & Fieser (John Wiley & Sons, 1967), pages 114 et seq. and 231 et seq.,respectively).

I claim:

1. A process suitable for introducing an amino group into the benzene or pyridine ring of a benzimidazole or imidazopyridine compound, which comprises reacting a first compound of one of the formulae

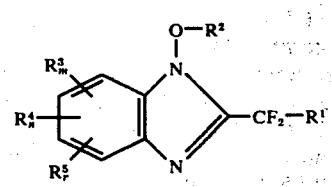

-continued

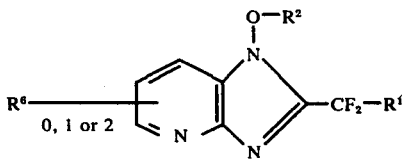

wherein
R¹ represents hydrogen, chloro, fluoro, perfluoroalkyl of $C_1$–$D_6$, or radical of the formula

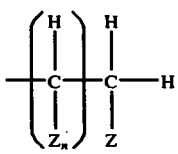

where each Z represents hydrogen or halo and n represents 0 or 1;
R² represents
1. alkyl of $C_1$–$C_8$;
2. alkenyl of $C_2$–$C_8$;
3. cycloalkyl of $C_5$–$C_6$;
4. benzyl;
5. phenethyl; or
6. tetrahydro-2-pyranyl;
each R³ independently represents halo;
each R⁴ independently represents nitro, —$CF_3$, —$CF_2Cl$, or —$CF_2H$;
R⁵ represents cyano or loweralkylsulfonyl of $C_1$–$D_4$;
m represents an integer of from 0 to 3, both inclusive;
n represents an integer of from 0 to 2, both inclusive;
r represents 0 or 1;
and the sum of m, n, and r is an integer of from 0 to 3, both inclusive, and
each R⁶ represents halogen, nitro, —$CF_3$, —$CF_2Cl$, —$CF_2H$, or loweralkylsulfonyl of $C_1$–$C4$, subject to the limitation that not more than one R⁶ represents nitro, —$CF_3$, —$CF_2Cl$, —$CF_2H$, or loweralkylsulfonyl as defined; with a nucleophilic reagent selected from the group consisting of ammonia, and primary and secondary amines having a $K_b$ from $10^{-2}$ to $10^{-11}$.

2. The process of claim 1 wherein the nucleophilic reagent is ammonia.

3. The process of claim 1 wherein the nucleophilic reagent is tert-butylamine.

4. The process of claim 1 wherein the nucleophilic reagent is n-propylamine.

5. The process of claim 1 wherein the first compound is 1-methoxy-6-chloro-2-(trifluoromethyl)-1H-imidazo-[4,5-b] pyridine.

6. The process of claim 5 wherein the nucleophilic reagent is ammonia.

7. The process of claim 5 wherein the nucleophilic reagent is tert-butylamine.

8. The process of claim 5 wherein the nucleophilic reagent is n-propylamine.

9. The process of claim 1 wherein the first compound is 1-methoxy-4,6-dinitro-2-(trifluoromethyl) benzimidazole.

10. The process of claim 9 wherein the nucleophilic reagent is ammonia.

11. The process of claim 9 wherein the nucleophilic reagent is tert-butylamine.

12. The process of claim 9 wherein the nucleophilic reagent is n-proplyamine.

* * * * *

UNITED STATES PATENT OFFICE
CERTIFICATE OF CORRECTION

Patent No. 4,031,107          Dated   June 21, 1977

Inventor(s)  George O.P. O'Doherty

It is certified that error appears in the above-identified patent and that said Letters Patent are hereby corrected as shown below:

Column 1, line 8:  "525,233" should read --535,233--.

Column 1, line 23:  "son" should read --on--.

Column 2, line 62:  "$C_5$-$5_6$" should read --$C_5$-$C_6$--.

Column 4, line 36:  "to" should read --or--.

Column 4, line 42:  "$CF_2cl$" should read --$CF_2Cl$--.

Column 4, line 49:  "1-methoxy4," should read --1-methoxy-4,--.

Column 6, line 14:  "$Y^-$" should read --$Y^\ominus$--.

Column 6, line 26:  "$Y^-$" should read --$Y^\ominus$--.

Column 6, line 39:  "-" should read -- $\ominus$ --.

Column 6, line 45:  "-" should read -- $\ominus$ --.

Column 6, line 68:  "productsM13" should read --products--.

Column 8, line 24:  "280°" should read --228°--.

Column 8, line 48:  "10milliliters" should read --10 milliliters--.

Column 10, line 22:  "6nitro" should read --6-nitro--.

Column 10, line 35:  "1-H" should read --1H--.

Column 10, line 61:  "benzimidazol"  should read --benzimidazole--.

UNITED STATES PATENT OFFICE
CERTIFICATE OF CORRECTION

Patent No. 4,031,107          Dated June 21, 1977

Inventor(s) George O.P. O'Doherty

It is certified that error appears in the above-identified patent and that said Letters Patent are hereby corrected as shown below:

Column 10, line 62: "150mg." should read --150 mg.--.

Column 11, line 64: "or" should read --on--.

Column 13, line 12: "$C_1-D_6$" should read --$C_1-C_6$--.

Column 13, line 34: "$C_1-D_4$" should read --$C_1-C_4$--.

Column 14, line 11: "$10^-11$" should read --$10^{-11}$

Signed and Sealed this

Eighth Day of November 1977

[SEAL]

Attest:

RUTH C. MASON
*Attesting Officer*

LUTRELLE F. PARKER
*Acting Commissioner of Patents and Trademarks*